US012153003B2

(12) United States Patent
Chen et al.

(10) Patent No.: US 12,153,003 B2
(45) Date of Patent: Nov. 26, 2024

(54) METHOD TO DETERMINE A MASS OF AN ABSORBED GAS AND A MASS OF A PORE GAS IN A SAMPLE

(71) Applicant: ARAMCO SERVICES COMPANY, Houston, TX (US)

(72) Inventors: Jin-Hong Chen, Katy, TX (US); Stacey M. Althaus, Houston, TX (US); Mohammed Boudjatit, El Kennar (DZ); Houzhu Zhang, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 197 days.

(21) Appl. No.: 17/937,309

(22) Filed: Sep. 30, 2022

(65) Prior Publication Data

US 2024/0118224 A1   Apr. 11, 2024

(51) Int. Cl.
*G01N 24/08* (2006.01)
*E21B 7/04* (2006.01)
(Continued)

(52) U.S. Cl.
CPC ............ *G01N 24/081* (2013.01); *E21B 7/04* (2013.01); *E21B 47/022* (2013.01);
(Continued)

(58) Field of Classification Search
CPC ...... G01N 24/00; G01N 24/08; G01N 24/081; G01N 33/00; G01N 33/24; G01N 33/241;
(Continued)

(56) References Cited

U.S. PATENT DOCUMENTS 4,295,365 A    10/1981   Meshri
9,482,631 B2   11/2016   Yang et al.
(Continued)

FOREIGN PATENT DOCUMENTS

CN    109856031 A   *   6/2019    ............ G01N 24/08
JP    2011085564 A  *   4/2011    ............ G01N 24/08

OTHER PUBLICATIONS

R. G. Loucks et al.; "Morphology, Genesis, and Distribution of Nanometer-Scale Pores in Siliceous Mudstones Of The Mississippian Barnett Shale", Journal of Sedimentary Research; vol. 79; 2009; pp. 848-861 (14 pages).
(Continued)

*Primary Examiner* — Hoai-An D. Nguyen
(74) *Attorney, Agent, or Firm* — Osha Bergman Watanabe & Burton LLP

(57) ABSTRACT

A method and system for determining a mass of an absorbed gas and a mass of a pore gas in a sample using NMR spectroscopy is provided. The method includes acquiring a baseline NMR spectrum of a pressure cell containing the sample, saturating the sample with a gas, acquiring a saturated NMR spectrum and determining a differential NMR spectrum of the sample by subtracting the baseline NMR spectrum from the saturated NMR spectrum. The method also includes separating the differential NMR spectrum into an absorbed gas NMR spectrum to determine an absorbed gas NMR signal and a pore gas NMR spectrum to determine a pore gas NMR signal by performing a spectral deconvolution. The method further includes acquiring a normalization NMR spectrum of the pressure cell containing a gas to determine a gas calibration NMR signal and determining the mass of the absorbed gas and pore gas.

20 Claims, 7 Drawing Sheets

(51) Int. Cl.
*E21B 47/022* (2012.01)
*G01N 33/24* (2006.01)
(52) U.S. Cl.
CPC ......... *G01N 33/241* (2013.01); *G01N 33/246* (2013.01); *E21B 2200/20* (2020.05)
(58) Field of Classification Search
CPC ...... G01N 33/246; G01R 33/00; G01R 33/20; G01R 33/44; G01R 33/46; G01R 33/4625; E21B 7/00; E21B 7/04; E21B 47/00; E21B 47/02; E21B 47/022; E21B 2200/00; E21B 2200/20
USPC .................................................. 324/376, 377
See application file for complete search history.

(56) References Cited

U.S. PATENT DOCUMENTS

| | | | |
|---|---|---|---|
| 9,828,820 | B2 | 11/2017 | Gupta et al. |
| 10,139,461 | B2* | 11/2018 | Cohen .................... G01R 33/12 |
| 10,534,871 | B2 | 1/2020 | Pomerantz et al. |
| 2014/0091800 | A1 | 4/2014 | Fordham |
| 2018/0292477 | A1 | 10/2018 | Chen et al. |
| 2021/0140902 | A1 | 5/2021 | Badri et al. |
| 2021/0239632 | A1 | 8/2021 | Ali et al. |

OTHER PUBLICATIONS

M. Thommes et al.; "Physisorption of gases, with special reference to the evaluation of surface area and pore size distribution (IUPAC Technical Report)", Pure and Applied Chemistry; vol. 87; Issue 9-10; 2015; pp. 1051-1069 (19 pages).
K. S. W. Sing; "Reporting Physisorption Data for Gas/Solid Systems with Special Reference to the Determination of Surface Area and Porosity", Pure and Applied Chemistry; vol. 54; No. 11; 1982; pp. 2201-2218 (18 pages).
S. A. Mengal and R. A. Wattenbarger; "Accounting For Adsorbed Gas in Shale Gas Reservoirs", SPE-141085; Society of Petroleum Engineers; Sep. 2011; pp. 1-15 (15 pages).
T. Zhang et al.; "Effect of organic-matter type and thermal maturity on methane adsorption in shale-gas systems", Organic Geochemistry; vol. 47; Apr. 5, 2012; pp. 120-131 (12 pages).
J-H. Chen et al.; "Capillary Condensation and NMR Relaxation Time in Unconventional Shale Hydrocarbon Resources", SPWLA-2012-186; SPWLA 53rd Annual Logging Symposium; Jun. 16, 2012; pp. 1-9 (9 pages).
F. Javadpour et al.; "Nanoscale Gas Flow in Shale Gas Sediments", Journal of Canadian Petroleum Technology; vol. 46; Issue 10; Oct. 1, 2007; pp. 55-61 (7 pages).
S. Reza Etminan et al.; "Measurement of gas storage processes in shale and of the molecular diffusion coefficient in kerogen", International Journal of Coal Geology; vol. 123; Oct. 21, 2013; pp. 10-19 (10 pages).
X. Wang and J. Sheng; "Gas sorption and non-Darcy flow in shale reservoirs", Petroleum Science; vol. 14; Jul. 22, 2017; pp. 746-754 (9 pages).
Y. Pang et al.; "Experimental measurement and analytical estimation of methane adsorption in shale kerogen", Fuel; vol. 240; Mar. 15, 2019; pp. 192-205 (14 pages).
T. Schoenberger; "Guideline for qNMR Analysis", ENFSI; Issue 1; Jun. 11, 2019 (24 pages).
G. F. Pauli et al.; "Quantitive 1H NMR: Development and Potential of a Method for Natural Products Analysis", Journal of Natural Products; vol. 68; Issue 1; Dec. 29, 2004; pp. 133-149 (17 pages).
K. Mehr et al.; "Electronic Referencing Techniques for Quantitative NMR: Pitfalls and How to Avoid Them Using Amplitude-Corrected Referencing through Signal Injection", Analytical Chemistry; vol. 80; No. 21; Oct. 10, 2008; pp. 8320-8323 (4 pages).
Z. Gu et al.; "NMR Response of Methane in Gas Shale", URTeC: 2438441; Unconventional Resources Technology Conference; Aug. 1, 2016; pp. 797-801 (5 pages).
S. Berger and S. Braun; "Determination of Pulse-Duration", in: 200 and More NMR Experiments, A Practical Course; Wiley; Ch. 2; Jul. 2004; pp. 14-42 (29 pages).
S. Berger and S. Braun; "Routine NMR Spectroscopy and Standard Tests", in: 200 and More NMR Experiments, A Practical Course; Wiley; Ch. 3; Jul. 2004; pp. 43-90 (48 pages).
Z. Gu et al.; "NMR Response of Methane in Gas Shale", URTeC: 2438441; Unconventional Resources Technology Conference; Aug. 1, 2016; pp. 1-5 (5 pages).
International Search Report issued for international patent application No. PCT/US2023/028063, mailed Jun. 24, 2024 (6 pages).
Written Opinion issued for international patent application No. PCT/US2023/028063, mailed Jun. 24, 2024 (11 pages).
"Inert Lubricants," Retrieved Jun. 6, 2024, from the Internet: URL <https://www.chemrawmat.co.uk/download/halocarbonoilsbrochure.pdf> Figure 14 (11 pages).
Min, B., et al., "Investigation of high frequency 1D NMR to characterize reservoir rocks," Journal of Petroleum Science and Engineering, 2019 (4 pages).
Han, H., et al., "High pressure magnetic resonance imaging with metallic vessels," Journal of Magnetic Resonance, 2011 (4 pages).

* cited by examiner

METHOD TO DETERMINE A MASS OF AN ABSORBED GAS AND A MASS OF A PORE GAS IN A SAMPLE

BACKGROUND

In the petroleum industry, hydrocarbons are located in reservoirs far beneath the surface of the Earth. Wells are drilled into these reservoirs to access and produce the hydrocarbons. As a wellbore is created beneath the surface of the Earth, rock core samples or rock plug samples are often extracted and brought to the surface for examination. In conventional coring, a cylindrical section of rock is cut and removed from the path of the wellbore by a coring bit. A second coring technique, termed "sidewall coring", may also be used to extract a rock core sample. In sidewall coring, mechanical tools may use hollow rotary drills to cut through the sidewall rock formation producing "rotary sidewall cores". The rock core sample is often a source rock, including shale, that may be examined to determine a reservoir characteristic. A source rock is a rock that is rich in organic matter that is capable of producing hydrocarbons. Kerogen is the primary organic material found in shales and other sedimentary rocks. A reservoir characteristic may incorporate any of the characteristics pertinent to the reservoirs ability to store and produce hydrocarbons and may be input to reservoir modelers. Reservoir modelers are used to produce a reservoir model of a subterranean region of interest. A reservoir simulator may use the reservoir model to create a reservoir simulation of the behavior of rocks and fluids under various hydrocarbon recovery scenarios to find a drilling target.

One examination technique used on rock core samples to determine a reservoir characteristic is nuclear magnetic resonance (NMR) spectroscopy. NMR spectroscopy, or NMR, measures the interaction of nuclear spins of atoms within the sample, when placed in a powerful magnetic field. NMR spectroscopy can be used to determine several reservoir characteristics pertinent to reservoir characterization, including porosity, composition, water and hydrocarbon content, or an injected fluid behavior. These characteristics may be used by a reservoir model and the reservoir model may, in turn, be used by a reservoir simulator to determine an advantageous production technique for a drilling operation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relating to a method for determining a mass of an absorbed gas and a mass of a pore gas in a sample using NMR spectroscopy is provided. The method includes acquiring a baseline NMR spectrum of a pressure cell containing the sample, saturating the sample with a gas, acquiring a saturated NMR spectrum and determining a differential NMR spectrum of the sample by subtracting the baseline NMR spectrum from the saturated NMR spectrum. The method also includes separating the differential NMR spectrum into an absorbed gas NMR spectrum to determine an absorbed gas NMR signal and a pore gas NMR spectrum to determine a pore gas NMR signal by performing a spectral deconvolution. The method further includes acquiring a normalization NMR spectrum of the pressure cell containing a gas to determine a gas calibration NMR signal and determining the mass of the absorbed gas and pore gas.

In general, in one aspect, embodiments relate to a non-transitory computer readable memory having computer-executable instructions stored thereon that, when executed by a processor, perform steps for determining a mass of an absorbed gas and a mass of a pore gas in a sample using NMR spectroscopy is provided. The instructions also include steps for acquiring a baseline NMR spectrum of a pressure cell containing the sample, saturating the sample with a gas, acquiring a saturated NMR spectrum and determining a differential NMR spectrum of the sample by subtracting the baseline NMR spectrum from the saturated NMR spectrum. The instructions further include steps for separating the differential NMR spectrum into an absorbed gas NMR spectrum to determine an absorbed gas NMR signal and a pore gas NMR spectrum to determine a pore gas NMR signal by performing a spectral deconvolution. The instructions also provide steps for acquiring a normalization NMR spectrum of the pressure cell containing a gas to determine a gas calibration NMR signal and determining the mass of the absorbed gas and pore gas.

In general, in one aspect, embodiments relate to a system that includes a pressure cell, a sample configured to be inserted into the pressure cell and an NMR pressure and injection system configured to establish a predetermined measurement pressure within the pressure cell and create a gas saturated sample in the pressure cell. The system further includes an NMR control and data acquisition system configured to acquire a baseline NMR spectrum of the pressure cell containing the sample, acquire a saturated NMR spectrum of the pressure cell containing the gas saturated sample and determine a differential NMR spectrum of the sample by subtracting the baseline NMR spectrum from the saturated NMR spectrum. The NMR control and data acquisition system is further configured to separate the differential NMR spectrum into an absorbed gas NMR spectrum and a pore gas NMR spectrum by performing a spectral deconvolution, determine an absorbed gas NMR signal based on the absorbed gas NMR spectrum and determine the pore gas NMR signal based on the pore gas NMR spectrum. The NMR control and data acquisition system is also configured to acquire a normalization NMR spectrum of the pressure cell containing the gas saturated sample, determine a gas calibration NMR spectrum based on the normalization NMR spectrum and determine a gas calibration NMR signal based on the normalization NMR spectrum. The NMR control and data acquisition system is also configured to determine a mass of an absorbed gas and a mass of a pore gas based on the absorbed gas NMR signal, the pore gas NMR signal and the gas calibration NMR signal and determine a reservoir characteristic of the sample based on the mass of the absorbed gas and the mass of the pore gas.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
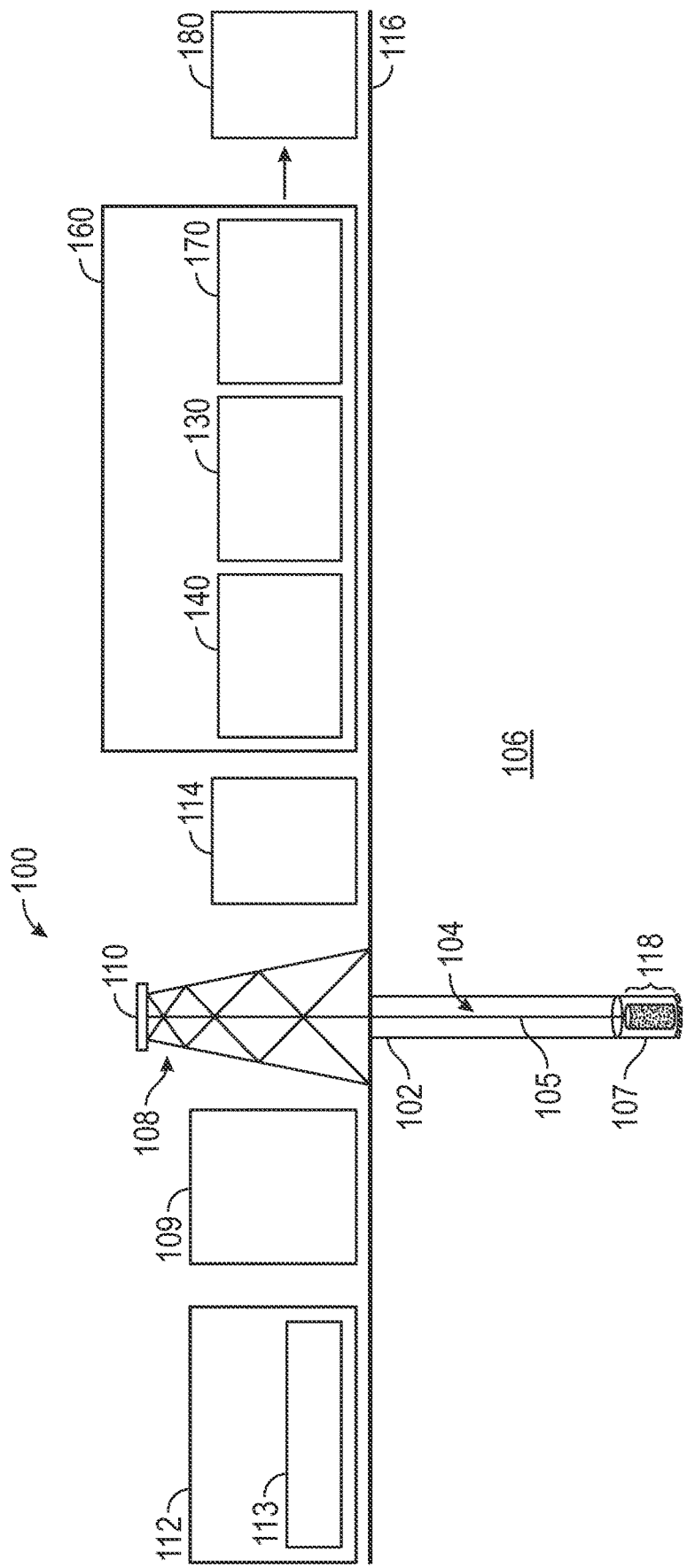
FIG. 1 depicts a well site in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-6 any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

The embodiments disclosed herein describe a method of determining a mass of an absorbed gas and a mass of a pore gas in a sample using NMR spectroscopy. A pore gas describes a gas that exists within the pore space of a rock core sample and adsorbed on the surface of the pore walls. The quantity of pore gas measured in a rock core sample is pertinent to determining a reservoir characteristic, including a porosity, to evaluate a reservoirs ability to store and produce hydrocarbons. A rock may also include an absorbed gas however, which describes a gas that has been absorbed or dissolved into the kerogen matrix of a rock core sample. An absorbed gas does not indicate a porosity, as this gas is dissolved into the kerogen matrix only and does not exist within the rock grains or pore space of the rock core sample. Traditionally, laboratory gas-adsorption measurements have been used to determine the porosity of unconventional reservoirs, including shale formations. In these traditional methods, a hydrocarbon fluid may be injected into a sample at a predetermined measurement pressure and the sample is evaluated for mass or volumetric changes to determine the quantity of gas that was successfully injected into the sample. These traditional methods may be used to determine the combined quantities of pore gas and absorbed gas, however, are unable to determine the relative amounts, which may lead to over-estimating the porosity of a sample. For source rocks such as shales, characterized by a low porosity and a higher percentage of a kerogen matrix, this over-estimation may be exacerbated.

Embodiments disclosed herein describe a method based on spectral deconvolution of a calibrated NMR spectrum for accurately determining the mass of the pore gas and the mass of the absorbed gas in a sample. By differentiating the mass of the absorbed gas from the mass of the pore gas, a more reliable reservoir characteristic, including a porosity may be determined. One or more reservoir characteristics may be used for reservoir evaluation. The reservoir characteristic may be used by a reservoir modeler to produce a reservoir model, which may include information about the total hydrocarbon in place and how effectively the hydrocarbons can potentially flow through the formation. The reservoir model may be used by a reservoir simulator to produce a reservoir simulation that predicts the behavior of rocks and fluid under various hydrocarbon recovery scenarios. A drilling target may be determined based on the reservoir simulation and a wellbore path may be planned using a wellbore path planning system based at least in part, on the drilling target. A wellbore may then be drilled guided by the wellbore path using a drilling system, in accordance with one or more embodiments.

FIG. 1 depicts a well site (100) in accordance with one or more embodiments, that may include a well (102) having a wellbore (104) extending into a formation (106). The wellbore (104) may include a bored hole that extends from the surface (116) into a target zone of the formation (106), such as a reservoir (not shown). The well site (100) may include a drilling system (108), a logging system (112), a control system (114), a reservoir modeler (160) and a reservoir simulator (180).

The drilling system (108) may include a well (102), a mud circulation system (109) to inject drilling fluids into the wellbore (104) and a coring bit (107) attached by a drillstring (105) to a coring rig (110). The formation (106) may be cored to produce rock core samples (118) or rock plug sample for analysis. Coring operations may include physically extracting a rock core sample (118) from a region of interest within the wellbore (104) by a coring bit (107) and bring it to Earth's surface (116) to be examined. The rock core samples (118), usually cylindrical, may be analyzed in a laboratory to determine various reservoir characteristics (130) from the location from which the sample was obtained.

The rock core sample (118) may be examined to determine a variety of reservoir characteristics (130) relevant to reservoir characterization including porosity, permeability, or the presence of hydrocarbons. Porosity may indicate how much void space or pore space exists in a particular rock within the formation (106), where oil, gas or water may be trapped. Permeability may indicate the ability of liquids and gases to flow through the rock within the area of interest.

The rock core samples (118) may be examined at the well site (100) or sent to a laboratory to perform different analyses, including NMR spectroscopy, to determine a reservoir characteristic (130). The control system (114) may include hardware and/or software for managing drilling operations and/or maintenance operations. For example, the control system (114) may include one or more programmable logic controllers (PLCs) that include hardware and/or software with functionality to control one or more processes performed by the drilling system (108).

The logging system (112) may include one or more logging tools (113), such as a nuclear magnetic resonance (NMR) logging tool or a resistivity logging tool, for use in generating well logs (140) of the formation (106). For example, a logging tool may be lowered into the wellbore (104) to acquire measurements as the tool traverses a depth interval. The plot of the logging measurements versus depth may be referred to as a "log" or "well log". Well logs (140) may provide depth measurements of the well (102) that describe such reservoir characteristics as formation porosity, formation permeability, resistivity, water saturation, and the like. The resulting logging measurements may be stored or processed or both, for example, by the control system (114), to generate corresponding well logs (140) for the well (102).

NMR logging measures the induced magnetic moment of hydrogen nuclei (specifically, protons) contained within the fluid-filled pore space of porous media (for example, reservoir rocks). Thus, NMR logs may measure the magnetic response of fluids present in the pore spaces of the reservoir rocks. In so doing, NMR logs may measure both porosity and permeability as well as the types of fluids present in the pore spaces, which is important for reservoir.

In some embodiments, a reservoir modeler (160) comprises functionality for simulating the flow of fluids, including hydrocarbon fluids such as oil and gas, through a formation composed of porous, permeable reservoir rocks. The reservoir modeler (160) may combine information determined from well logs (140), reservoir characteristics (130) determined from rock core samples (118) and any other geological models (170) available to build models of the reservoir. The reservoir models may include information total hydrocarbon in place, where the hydrocarbons are located, and how effectively the hydrocarbons can potentially flow.

In some embodiments, a reservoir simulator (180) may be configured to accept a reservoir model and produce a reservoir simulation to predict the behavior of rocks and fluid under various hydrocarbon recovery scenarios, allowing reservoir engineers to understand which recovery options offer the most advantageous hydrocarbon recovery plan for a given reservoir. A drilling target, or a chosen location to penetrate the hydrocarbon reservoir, may be determined through reservoir simulation by estimating the fluid flow within the reservoir given various drilling target scenarios.

The reservoir simulator (180) may include hardware and/or software with functionality for performing one or more reservoir simulations regarding the hydrocarbon-bearing formation (106). Drilling decisions may be made on the well site (100), including determining an updated drilling target, based at least part, on the reservoir simulation. While the reservoir modeler (160) and reservoir simulator (180) are shown at a well site (100), in some embodiments, the reservoir modeler (160) and the reservoir simulator (180) may be remote from a well site. In some embodiments, the reservoir modeler (160) is implemented as part of a software platform for the control system (114). The software platform may obtain data acquired by the drilling system (108) and logging system (112) as inputs, which may include multiple data types from multiple sources. The software platform may aggregate the data from these systems (108, 112) in real time for rapid analysis. In some embodiments, the control system (114), the logging system (112), the reservoir modeler (160) and/or the reservoir simulator (180) may include a computer system that is similar to the computer system (702) described below with regard to FIG. 7 and the accompanying description.

The rock core sample (118) may be examined to determine a variety of reservoir characteristics (130) relevant to reservoir characterization including porosity, permeability, or the presence of hydrocarbons. Porosity may indicate how much void space or pore space exists in a particular rock within the formation (106), where oil, gas or water may be trapped. Permeability may indicate the ability of liquids and gases to flow through the rock within the area of interest. The rock core samples (118) may be examined at the well site (100) or sent to a laboratory to perform different analyses, including NMR spectroscopy, to determine a reservoir characteristic (130). NMR or NMR spectroscopy is one valuable analysis technique used on a variety of different sample objects in a variety of industries. NMR is the study of molecules by recording the interaction of radiofrequency (Rf) electromagnetic radiations with the nuclei of molecules placed in a strong magnetic field, using an NMR system.

Figure 2:
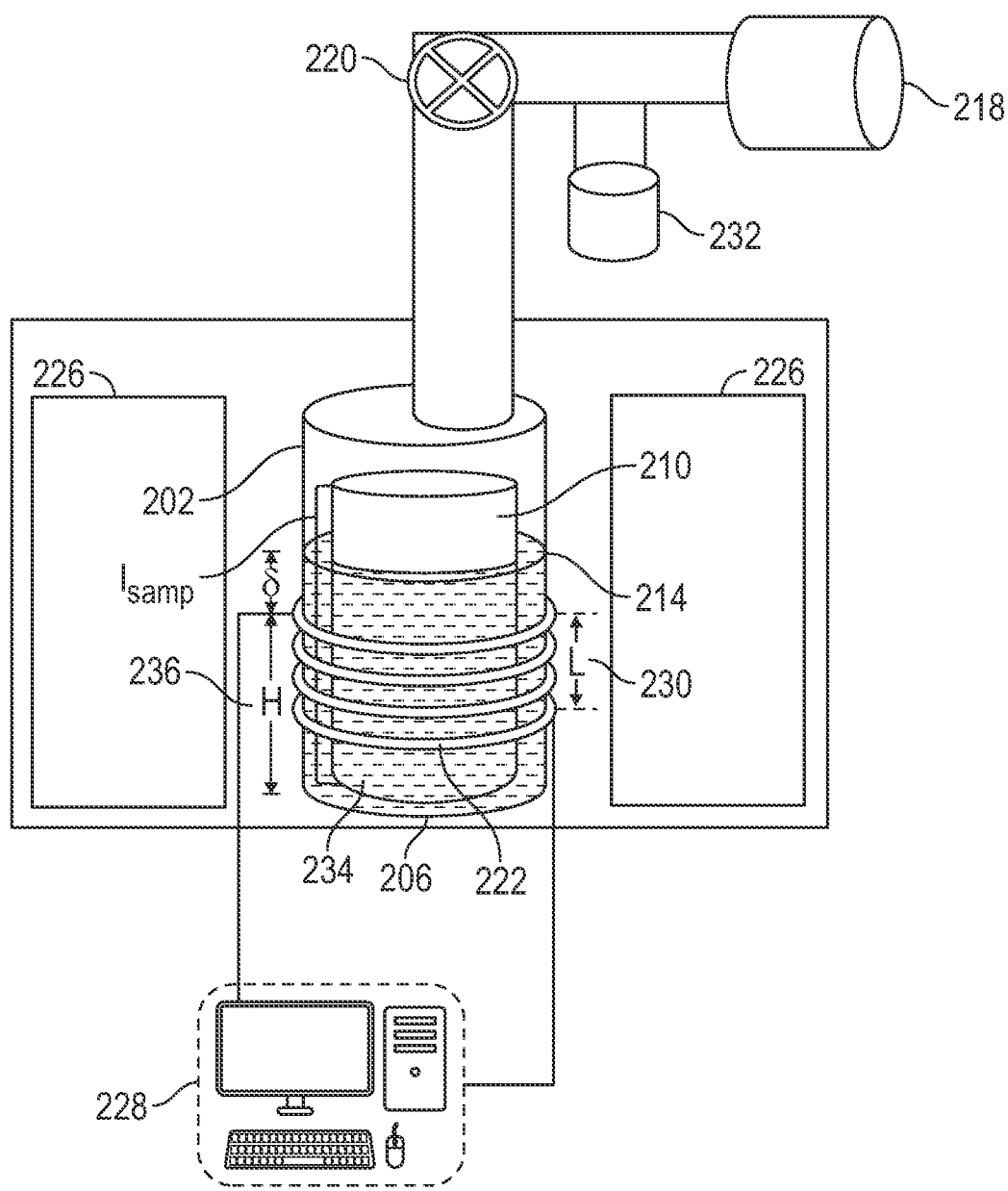
FIG. 2 depicts an NMR system in accordance with one or more embodiments.

FIG. 2 depicts an NMR system (200) in accordance with one or more embodiments. Before a sample (210) is examined in pressurized NMR analyses using the NMR system (200), it may be inserted inside the pressure cell (202). A pressure cell (202) may house the sample (210) and withstand an elevated measurement pressure during NMR analyses. The sample (210) may be a rock core sample, extracted from a subterranean region of interest by coring, as described by FIG. 1. This rock core sample may be a source rock, including shales containing a kerogen matrix, that may be examined to determine a reservoir characteristic.

The NMR system (200) includes a superconducting magnet or magnets (226). The superconducting magnets (226) may be two separate magnets as shown in FIG. 2, or one large magnet with a center opening, allowing for the insertion of the pressure cell (202). During traditional NMR analyses, the sample (210) located inside the pressure cell (202) is placed in the center of the superconducting magnet (226) as shown in FIG. 2. The NMR system (200) also includes an NMR coil (222), with a sensitive region (230). The NMR coil (222) is only sensitive to NMR measurements between this length shown on the sensitive region (230) shown in FIG. 2. The NMR coil (222) is magnetic and generates a magnetic field whenever a current flows through it. The NMR coil (222) is used to irradiate radiofrequency pulses and to detect and collect the NMR signal emitted by the sample (210).

When molecules of a sample (210), at an initial equilibrium state, are placed in a strong magnetic field, as in standard NMR spectroscopy techniques, the nuclear spins of some atoms (such as the proton forming a hydrogen $^1$H nucleus) will behave like small magnets and become aligned. If a broad spectrum of radio frequency waves is applied to the sample (210), or an Rf pulse, the nuclei will begin to resonate at their own specific frequencies or resonant frequencies. This is called magnetic resonance and is achieved when the nuclei are irradiated with radiofrequency. The Rf pulse, which may be generated by an NMR coil (222), is then switched off, and the molecules return to their initial equilibrium state, which produces a magnetization. This magnetization will induce an alternating current (AC) in the NMR coil (222).

Figure 4A:
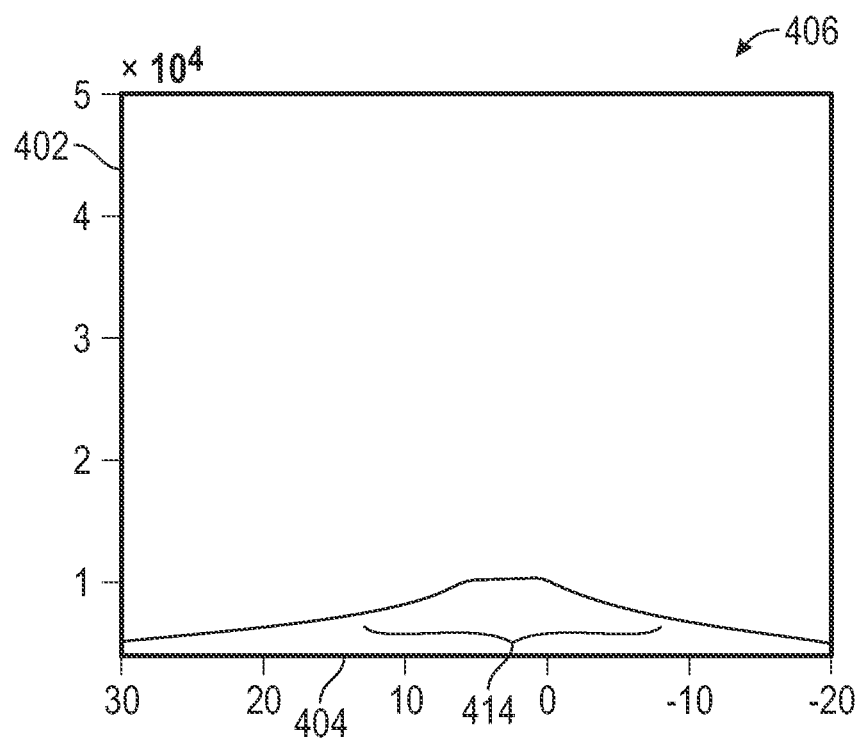
FIGS. 4A-4C show NMR spectra in accordance with one or more embodiments.
Figure 4B:
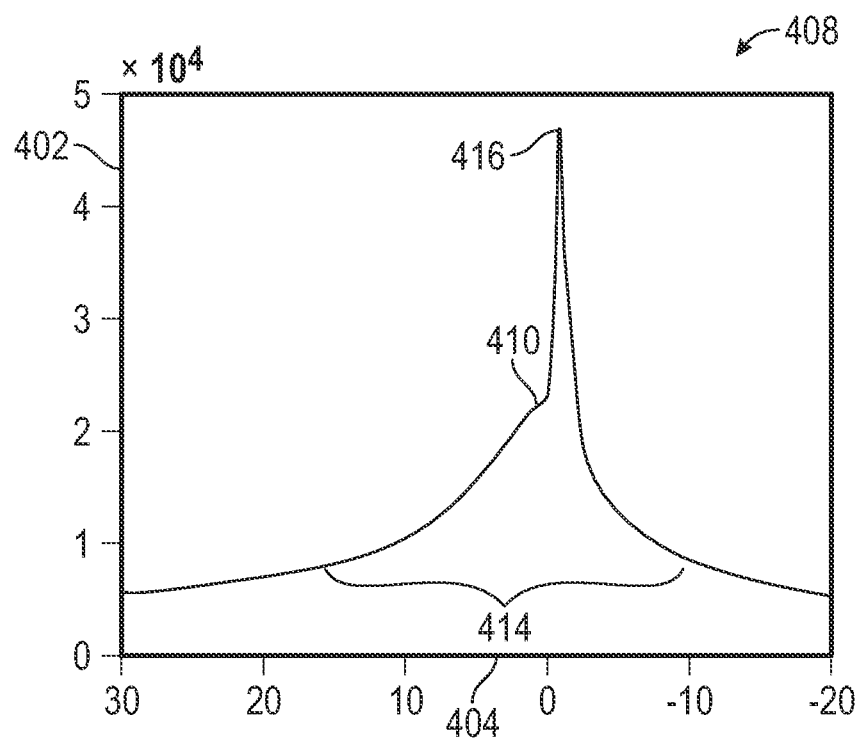
Figure 4C:
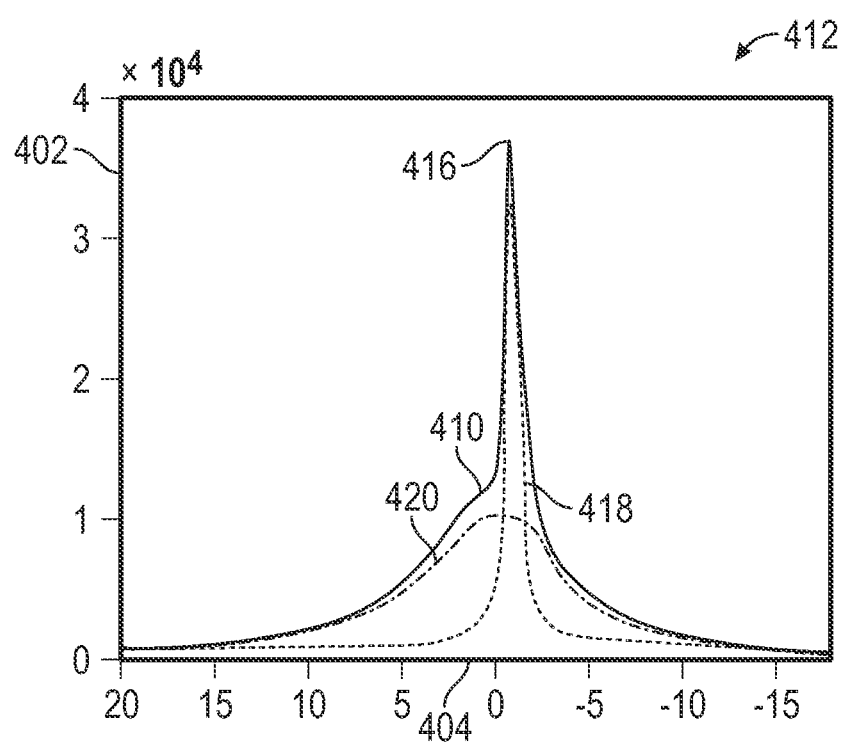

This induced AC in the NMR coil (222) is measurable and referred to as the free induction decay (FID). The FID contains the NMR signal produced from NMR spectroscopy, however it is difficult to interpret in the time domain. The FID is transformed, using a Fourier transformation, into a plot of intensities versus frequencies known as an NMR spectrum. In other words, FID is the directly measured NMR signal, and the NMR spectrum is a Fourier transform of the acquired FID. An NMR spectrum may reveal valuable reservoir characteristics pertinent to the sample (210) being measured and is illustrated in FIGS. 4A-4C.

The NMR control and data acquisition system (228) is responsible for data acquisition and subsequent mathematical transformation into this interpretable NMR spectrum. The NMR control and data acquisition system (228) may record the observable NMR signal, or FID that is generated by the NMR system (200). The NMR control and data acquisition system (228) may include a monitor to display and process the NMR spectrum that is created. The NMR control and data acquisition system (228) may include a computer system that is similar to the computer system (602) described below with regard to FIG. 6 and the accompanying description. The computer system may be used to process the NMR spectrum, including performing a Fourier transformation on the FID to create the NMR spectrum, performing curve fitting on the NMR spectrum, and determining the peak integration or integration of the NMR peak on the NMR spectrum. An integration is performed in NMR spectroscopy to determine the NMR signal of a sample (210).

The location of the curve or peak of the NMR response on the NMR spectrum, in relation to a benchmark, is called the chemical shift. The chemical shift is defined by the frequency of the resonance expressed with a reference to this benchmark or standard. The position and number of chemical shifts may be diagnostic of the structure of the sample (210) being analyzed. The most common isotopes used to detect NMR signals are $^1$H and $^{13}$C, however many others may be used. For NMR experiments measuring $^1$H, Tetramethylsilane [TMS;(CH$_3$)$_4$Si] is generally used for this benchmark to determine chemical shift of compounds: $\delta_{TMS}=0$ ppm. That is, chemical shift is represented as parts per million (ppm) relative to Tetramethylsilane. A sample's chemical shift may also be indicative of several factors relating to a reservoir characteristic, including estimating a porosity and viscosity.

NMR spectroscopy is routinely used to study the fluid distribution and transport in the pore networks in rock core samples. Many of these studies are required to be at reservoir conditions at pressures that reach more than 10 thousand PSI. An injected fluid (218), may be injected into the pressure cell (202) by an NMR pressure and injection system (220), to establish the desired predetermined measurement pressure. The injected fluid (218) may be a hydrocarbon gas including methane. Methane may be used to represent one of the many hydrocarbon gases that are typically used to establish this desired measurement pressure. The injected fluid (218) may also be a combination of hydrocarbon gases in accordance with one or more embodiments. The injected fluid (218) used in NMR analyses is dependent on the interest of study and may be chosen to determine the behaviour of that specific injected fluid (218) within the pores of the sample (210). By choosing a hydrocarbon gas such as methane to be injected at a predetermined measurement pressure, NMR analyses may represent reservoir conditions that may indicate the hydrocarbon fluid distribution and transport in the pore networks in a rock core sample.

An NMR system (200) may include a vacuum pump (232) that may be used to vacuum the sample (210) to remove any removable fluids from the sample (210) prior to the injection of a hydrocarbon gas. A rock core sample may be vacuumed to remove any fluids that may be present inside the pore space or on the surface of the sample (210). By removing the fluid trapped in the pore space prior to NMR analysis, the pore space is now free to accept a hydrocarbon gas that may be injected using the NMR pressure and injection system (220). An NMR system (200) may include additional features or omit any mentioned features in accordance with one or more embodiments, without departing from the novel aspect of the method.

In NMR spectroscopy, the area under a peak seen at the chemical shift on an NMR spectrum is proportional to the number of atoms that gave rise to that signal. The NMR control and data acquisition system (228) may be used to determine the area under the peak or peaks on the NMR spectrum by performing an integration or a peak integration. Determining the area under the NMR signal may indicate the amount hydrocarbon gas that was injected into the pore space of a sample (210), indicating a porosity. NMR spectroscopy can detect the NMR response from the injected gas both inside the pore space and adsorbed on the pore wall surface of the sample (210), referred to as the pore gas. For rock core samples, such as shales that possess a kerogen matrix however, a hydrocarbon gas injected at a reservoir pressure may also dissolve or diffuse into the kerogen matrix, resulting in an absorbed gas. The NMR response from the absorbed gas can overlap with the signal from the pore gas, making the study of pore fluid very difficult if not impossible.

In a traditional NMR analyses, a sample (210) is loaded in a pressure cell (202) and placed in an NMR coil (222) of the NMR system (200). In this design, an annular space or interior volume exists between the sample (210) and the inner wall of the pressure cell. This interior volume is shown in FIG. 2 being occupied by a volume of filler fluid (234), however during traditional NMR analyses, the interior volume is empty. When an injected fluid (218) is injected into the sample (210) inside the pressure cell (202) it also fills this interior volume. The injected fluid (218) in the interior volume produces a measureable NMR response. This NMR response from the interior volume fluid can overlap with the signal from the sample (210) and makes the study of the pore fluid very difficult, if not impossible. This overlap in NMR signals corrupt the NMR response obtained and may give inaccurate information as to a samples porosity, permeability, or other characteristics. To ensure that there is no NMR response from the injected fluid (218) inside the interior volume of the pressure cell, the addition of a filler fluid (234) may be introduced into the NMR system (200).

The filler fluid (234) comprises a hydrogen-free fluid, including Halocarbon 1000N. The filler fluid (234) may be any fluid that has a negligible NMR response or no NMR response during NMR analyses. The filler fluid (234) may be injected into the pressure cell (202) at a first temperature, which ensures a sufficiently low viscosity to allow for the injection process. The viscosity of the filler fluid (234) at the first temperature may be between 5 centipoise (cp) and 500 cp in order to ensure a successful injection. The filler fluid may be injected into the pressure cell (202) by a syringe, a pipette, or by any other means. For example, the syringe may be a long needle syringe. Similarly, the pipette may be a narrow tip pipette.

The volume of filler fluid (234) may be selected in conjunction with the interior diameter of the pressure cell and the exterior diameter of the sample so that the surface of the filler fluid (234) reaches the predetermined level (214) when the sample (210) is fully inserted into the pressure cell (202). The predetermined level (214) is defined by having a final height relationship H+δ, shown in FIG. 2, wherein H is the distance from the closed end (206) of the pressure cell (202) to the top NMR coil surface (236), and δ is the distance from the top of H to the predetermined level (214) within the interior volume of the pressure cell. The final height of the filler fluid (234) at the predetermined level (214) must be higher than a top NMR coil surface (236). The top NMR coil surface (236) marks the end of the sensitive region (230) of the NMR coil (222). Secondly, the height of the filler fluid (234) at the predetermined level (214), or H+δ, must also be smaller than the length of the sample, $l_{samp}$, so that injected fluids (218) may be injected into the sample (210) from the top of the pressure cell (202) to study the samples injections with the injected fluids (218). No empty interior volume is shown within the NMR coil (L) sensitive region (230), therefore no NMR response is expected from injected fluids (218) in the interior volume of the pressure cell during NMR analyses. Based on the criteria given, the filler fluid volume (234) is determined by:

$$v=[\pi(d_{cell}^{ID}/2)^2-\pi(d_{samp}/2)^2]\times(H+\delta)$$  Equation (1)

where $H+\delta<l_{samp}$. Therefore, determining a volume of filler fluid, is determining the volume of filler fluid required to reach a predetermined level (214) within the interior volume of the pressure cell, when displaced by a sample (210). The volume of filler fluid (234) at the predetermined level (214), is illustrated in FIG. 2.

Prior to the insertion of the sample (210) into the pressure cell (202) and the displacement of a portion of the volume of filler fluid (234) the volume of filler fluid (234) may be brought to a second temperature. At the second temperature, that may typically be a lower temperature than the first temperature, the viscosity of the filler fluid (234) may be higher than its viscosity at the first temperature. Consequently, the filler fluid (205) may resist flow under a pressure gradient. In particular, when a rock core sample is used, or other samples (210) that contain pores, the filler fluid (205) at the second temperature may resist flow into the pores of a porous sample. Bringing the filler fluid (234) to a second temperature and thus an increased viscosity, prevents or strongly inhibits, the flow of filler fluid (205) into the pores of the sample (210). Any method to change the temperature of the filler fluid (234) to a second temperature inside the pressure cell (202) may be used, including placing the pressure cell (202) containing the filler fluid (234) in a cooler to speed the process.

With the volume of filler fluid (234) at a second temperature, the sample may be inserted into the volume of filler fluid (234) within the pressure cell (202), displacing an upper surface of filler fluid to a predetermined level (214) within the interior volume of the pressure cell, in accordance with one or more embodiments. The sample is inserted through an open end of the pressure cell into the filler fluid (234) disposed at a closed end (206) of the pressure cell (202). This predetermined level (214) is determined so that the filler fluid, having a negligible NMR response, occupies the portion of the interior volume of the pressure cell, that is readable by the sensitive region (230) of the NMR coil (222). The length of the sample (210) being longer than the predetermined level (214) ensures successful injection of an experimental liquid or gas, into the pores of the sample (210). With the sample and filler fluid at a second temperature in the pressure cell (202), the pressure cell (202) may now be sealed at an open end and inserted into the center of the superconducting magnets (226). By replacing an otherwise empty annular space or interior volume with this hydrogen-free filler fluid having a negligible NMR response, the potential for injected fluids (218) to occupy this interior volume within the sensitive region (230) of an NMR coil (222), during NMR analyses may be reduced or eliminated.

Halocarbon 1000N may be used as the filler fluid and is an inert oil and more specifically a high molecular weight polymer of chlorotrifluoroethylene (PCTFE). Halocarbon contains no hydrogen and generates a negligible NMR response during NMR analyses. Halocarbon 1000N also displays a high range of viscosities dependent on temperature. For example, Halocarbon 1000N has a viscosity of 1000 cp at room temperature (approximately 22° Celsius (C)) but becomes much less viscous at higher temperatures and much more viscous at lower temperatures. Other types of fluids other than Halocarbon may also be used dependent on satisfying the NMR requirements. The first requirement is that the filler fluid cannot contain a detectable NMR signal. NMR experiments used in the study of rock core samples detect $^1H$ (hydrogen with a single atom), therefore the filler fluid must comprise of 'a hydrogen-free filler fluid' or a fluid that contains no hydrogen. The filler fluid must also be sufficiently viscous so that invasion into the rock core is negligible. NMR analyses on rock core samples often measure the NMR response of injected materials in the pore space of rocks. Therefore, the filler fluid must be sufficiently viscous, whenever in contact with the rock core sample, as to not intrude into the pore space. The addition of the filler fluid (234) as described in FIG. 2 may be included in the novel method, prior to measuring the NMR response of the sample in accordance with one or more embodiments.

Figure 3:
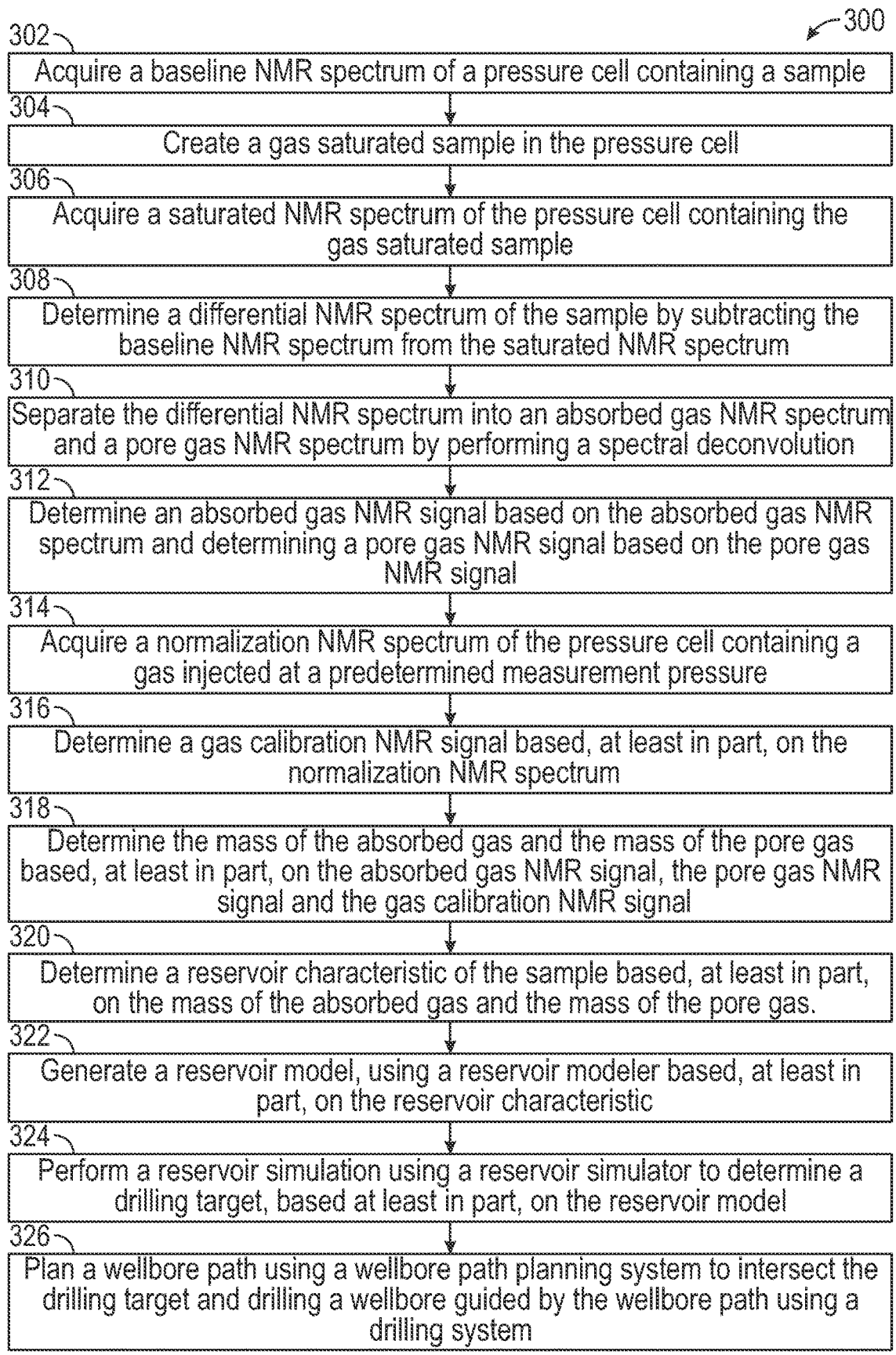
FIG. 3 shows a flowchart in accordance with one or more embodiments.

FIG. 3 shows a flowchart describing the method for determining a mass of an absorbed gas and a mass of a pore gas in a sample using nuclear magnetic resonance (NMR) spectroscopy. The sample may be a rock core sample, extracted from a subterranean region of interest by coring, as described by FIG. 1. This rock core sample may be a source rock, including shales with a kerogen matrix, that may be examined to determine a reservoir characteristic. The gas may be a hydrocarbon gas in accordance with one or more embodiments. By choosing a hydrocarbon gas such as methane to be injected into the pressure cell containing the rock core sample at a predetermined measurement pressure, NMR analyses may represent reservoir conditions that may indicate the hydrocarbon fluid distribution and transport in the pore networks in a rock core sample. Methane is a hydrocarbon gas commonly used in studies of this nature, although similar results may also be obtained using other hydrocarbon gases, such as ethane, and propane. A combination of hydrocarbon gases may also be used in accordance with one or more embodiments. The following embodiments described in FIG. 3 involve using an NMR system similar to the one described in FIG. 2.

In Step 302 a baseline NMR spectrum of the pressure cell containing the sample is acquired in accordance with one or more embodiments. The sample may be a rock core sample including shales with a kerogen matrix. The sample is placed inside the pressure cell and then placed in the center of the superconducting magnets of the NMR system as described in FIG. 2. A baseline NMR spectrum is acquired to determine the NMR response from a rock core sample that has a free pore space, or a pore space that is not occupied by any removable fluids. To ensure that the rock core sample has a free pore space, prior to measuring the NMR response, the sample is vacuumed to remove any fluids from the surface of the rock and from within the pore space of a sample. The sample may be vacuumed using a vacuum pump, an element of the NMR system described by FIG. 2.

The baseline NMR spectra is then acquired by using routine NMR methods, such as using a Rf pulse to excite the spin system. The subsequent FID is recorded and transformed into an interpretable baseline NMR spectrum by performing a Fourier transform using the NMR control and data acquisition system. The baseline NMR spectrum is acquired before any hydrocarbon gas is injected into the pressure cell and a predetermined measurement pressure is established. The baseline NMR spectrum represents the NMR response from the rock core sample with a free pore space and is illustrated and described further in FIG. 4A.

In Step 304 a gas saturated sample is created in the pressure cell in accordance with one or more embodiments. The sample becomes saturated by injecting a gas at the predetermined measurement pressure into the pressure cell containing the sample, until the saturated NMR spectrum stabilizes. The predetermined measurement pressure may represent a pressure the rock core sample is subjected to in a reservoir. By replicating a reservoir pressure in the NMR analyses, a more accurate reservoir characteristic may be determined. The gas may be a hydrocarbon gas, injected using the NMR pressure and injection system, which includes a pressure pump with a transducer for pressure control described in FIG. 2. By choosing a hydrocarbon gas such as methane to be injected at a predetermined measurement pressure representing a reservoir pressure, NMR analyses may represent reservoir conditions that may indicate the hydrocarbon fluid distribution and transport in the pore networks in a rock core sample. The injected hydrocarbon gas used as an example in the following equations represent methane, which was the hydrocarbon gas used to produce the NMR spectra seen in FIG. 4, but any gas or combination of gases may be used in accordance with one or more embodiments.

During the injection of the hydrocarbon gas (e.g., methane), the NMR spectrum may be observed. The NMR system is able to record an NMR response from the rock core sample and the gas that has been injected into the sample, during the active injection without interfering with the recorded NMR response. During the gas injection, multiple NMR spectra may be acquired to determine when the NMR signal experiences no intensity change. When there is no change of intensity in the NMR signal observed between two consecutive the NMR spectra, the NMR spectrum has stabilized, and the gas injection may be turned off. The stabilization of the NMR spectrum indicates that the hydrocarbon gas has completely occupied all available pore space of the rock core sample within the sensitive portion of the coil. In addition to this pore gas however, there is a portion of the injected hydrocarbon gas that becomes absorbed in the kerogen matrix of the sample, referred to as an absorbed gas.

In Step 306 a saturated NMR spectrum of the pressure cell containing the gas saturated sample is acquired in accordance with one or more embodiments. Once the hydrocarbon gas has been completely injected into the pore space of a rock core sample, indicated by a NMR spectrum stabilization, the NMR spectrum may be recorded with the gas injection shut off. While the saturated NMR spectrum may be obtained during the active injection of a hydrocarbon gas, an additional NMR spectrum is generally acquired after the injection has been stopped to further verify that no intensity change in NMR signal has occurred. The saturated NMR spectrum represents the NMR response of the rock core sample, the pore gas, and the absorbed gas in accordance with one or more embodiments. The combination of pore gas and absorbed gas is referred to as a total gas. Step 304 and Step 306 may be performed simultaneously in accordance with one or more embodiments. The NMR pressure and injection system may continue to inject a hydrocarbon gas into the sample, while the saturated NMR spectrum is analyzed to determine an intensity change. When there is no observable intensity change, the saturated NMR spectrum is recorded, and the NMR pressure and injection system may be shut off. A saturated NMR spectrum is illustrated and described further in FIG. 4B.

In Step 308 a differential NMR spectrum of the sample is determined by subtracting the baseline NMR spectrum from the saturated NMR spectrum in accordance with one or more embodiments. The baseline NMR spectrum represents the NMR response from the rock core sample only and the saturated NMR spectrum represents the NMR response from the combination of the rock core sample, the pore gas and the absorbed gas. By subtracting the baseline NMR spectrum from the saturated NMR spectrum, the NMR signal that remains, represents the NMR response of the pore gas and the absorbed gas only. The differential NMR spectrum is defined by:

$$M_{CH_4}^{core} = M_{ab} + M_p \quad \text{Equation (2)}$$

where $M_{CH_4}^{core}$ is the total NMR signal from the differential NMR spectrum and defined by the summation of the absorbed gas NMR signal $M_{ab}$ and the pore gas NMR signal $M_p$. The NMR control and data acquisition system may include a computer system capable of determining a differential NMR spectrum. A differential NMR spectrum is illustrated in FIG. 4C, resulting from the subtraction of a baseline NMR spectrum, described in Step 302 from the saturated NMR spectrum, described in Step 306.

In Step 310 the differential NMR spectrum is separated into an absorbed gas NMR spectrum and a pore gas NMR spectrum by performing a spectral deconvolution in accordance with one or more embodiments. The differential NMR spectrum contains an overlapping NMR response from the pore gas and absorbed gas. In order for the mass of the pore gas and the mass of the absorbed gas to be determined, these overlapping NMR responses must be separated, or deconvolved. The spectral deconvolution may be performed by the computer system included in the NMR control and data acquisition system, described in FIG. 2. The differential NMR spectrum illustrated in FIG. 4C consist of an overlapping NMR response that may be separated into a broad peak and a narrow peak. The broad peak seen on the differential NMR spectrum is the NMR response produced by the absorbed gas and the narrow peak is the NMR response produced by the pore gas in the rock core sample. The spectral deconvolution of the differential NMR spectrum is accomplished by curve fitting. Curve fitting describes the process of constructing a curve, or a mathematical function, that has the best fit to a series of datapoints representing the spectral line shape of the differential NMR spectrum. A nonlinear least squares curve fitting application may be used to fit the two peaks of the differential NMR spectrum to two Lorentzian curves, as the datapoints on the NMR spectrum is often best fit by a Lorentzian curve.

A first Lorentzian curve is fit to the broad peak of the differential NMR spectrum to obtain an absorbed gas NMR spectrum in accordance with one or more embodiments. The Lorentzian curve used to fit the broad peak is the absorbed gas NMR spectrum in accordance with one or more embodiments. A second Lorentzian curve is fit to the narrow peak of the differential NMR spectrum to obtain a pore gas NMR spectrum in accordance with one or more embodiments. The Lorentzian curve used to fit the broad peak is the pore gas NMR spectrum in accordance with one or more embodiments. Curve fitting may be performed manually by a user using the NMR control and data acquisition system or the NMR control and data acquisition system may include hardware or software with functionality for automated curve fitting. Other functions or shapes may be used to fit the two peaks of the differential NMR spectrum in accordance with one or more embodiments. For example, a Gaussian function or a Voigt function may be used. Two peaks on a differential NMR spectrum fit by two Lorentzian curves are illustrated in FIG. 4C in accordance with one or more embodiments.

In Step 312 an absorbed gas NMR signal is determined based, at least in part, on the absorbed gas NMR spectrum and a pore gas NMR signal is determined based, at least in part, on the pore gas NMR spectrum in accordance with one or more embodiments. In NMR spectroscopy, the area under the peak or curve on the NMR spectrum is proportional to the number of atoms that gave rise to that signal. The NMR control and data acquisition system may be used to determine the area under the broad peak of the absorbed gas NMR spectrum to determine the absorbed gas NMR signal. Conversely, the NMR control and data acquisition system may be used to determine the area under the narrow peak of the pore gas NMR spectrum to determine the pore gas NMR signal. Determining the area under the narrow curves seen on the pore gas NMR spectrum may indicate the amount of gas that was injected into the pore space of a sample, or pore gas, indicating a porosity.

For rock core samples, such as shales that possess a kerogen matrix however, a hydrocarbon gas injected at a reservoir pressure may also dissolve or diffuse into the kerogen matrix, resulting in an absorbed gas. The NMR response from the absorbed gas can overlap with the NMR response from the pore gas, making the study of pore fluid very difficult if not impossible. The measured NMR signal in the absorbed gas NMR spectrum and the pore gas NMR spectrum is proportional to the number of atoms that gave rise to that signal and thus the mass of the respective gas. For each component, we have:

$$M_{ab} = c_{NMR} \rho_{ab} \phi_{ab} \pi L d_{core}^2 / 4 \qquad \text{Equation (3)}$$

And $$M_p = c_{NMR} \rho_p \phi_p \pi L d_{core}^2 / 4 \qquad \text{Equation (4)}$$

where $c_{NMR}$ is a constant depending on the NMR instrument and acquisition parameters; $\rho_{ab}$ and $\rho_p$ are average density of absorbed methane and pore methane, respectively; $\phi_{ab}$ and $\phi_p$ are the volume fraction of absorbed methane and pore methane, respectively; $\pi L d_{core}^2/4$ is the plug volume in the NMR coil length L. $d_{core}$ is the diameter of the rock core sample used. The NMR response is only measurable in the sensitive region of the NMR coil L, so that is length component in determining the mass of an absorbed gas and the mass of the pore gas. The total methane NMR signal is:

$$M_{CH_4}^{core} = c_{NMR}(\rho_{ab}\phi_{ab} + \rho_p\phi_p)\pi L d_{core}^2/4 \qquad \text{Equation (5)}$$

In Step 314 a normalization NMR spectrum of a pressure cell containing a gas injected at a predetermined measurement pressure is acquired in accordance with one or more embodiments. The normalization NMR spectrum describes the spectrum acquired from a gas injected into an empty pressure cell. The same hydrocarbon gas used in determining the saturated NMR spectrum is injected at the same predetermined measurement pressure to determine the normalization NMR spectrum. The NMR system specifications remain constant throughout the NMR analyses, including the type and size of pressure cell, NMR coil, and Rf pulse used to excite the system.

Once the injected hydrocarbon gas has filled the interior of the pressure cell, indicated by the normalization NMR spectrum displaying no intensity change, the normalization NMR spectrum is recorded by the NMR control and data acquisition system. NMR measurements using NMR standards for a calibration are well known to those skilled in the art of NMR analysis. Different calibration techniques include internal standards, external standards, and electronic references. Any technique known to those skilled in the arts may be used to perform this calibration, the external standard method will be used as an example here. An external standard calibration describes the combination of known data from a calibration standard, or information determined from a normalization NMR spectrum and unknown data from the sample, which includes the bulk gas density or bulk methane density in this example.

In Step 316 a gas calibration NMR signal is determined based, at least in part, on the normalization NMR spectrum in accordance with one or more embodiments. The gas calibration NMR signal is determined by the same process used to determine the absorbed gas NMR signal and the pore gas NMR signal. The peak on the gas calibration NMR spectrum may be integrated to determine a gas calibration NMR signal in accordance with one or more embodiments. The acquired gas calibration NMR signal in the pressure cell, $M_{CH_4}^{O.C.}$, is proportional to the injected hydrocarbon gas within the NMR coil and may be written as:

$$M_{CH_4}^{O.C.} = c_{NMR} \rho_b \pi L (d_i^{o.c.})^2 / 4 \qquad \text{Equation (6)}$$

where $\rho^b$ is the bulk gas density at experimental temperature and pressure, $d_i^{o.c.}$ is the inner diameter of the pressure cell. Steps 314 and 316 may also be performed sequentially prior to performing Step 302 in accordance with one or more embodiments. The variable $c_{NMR}$ in equation 6 is the same constant relating to the NMR instrument and acquisition parameters used in equations 2-5. The variable $c_{NMR}$ may be first determined by solving the gas calibration NMR signal given by equation 6 to be used in equations 2-5 in accordance with one or more embodiments. An additional NMR system having the same equipment and experimental parameters may be used to perform Steps 314 and 316. In the circumstance where two separate NMR systems are used, Steps 314 and 316 may be performed in parallel with Steps 302-312 on a separate NMR system.

In Step 318 the mass of the absorbed gas and the mass of the pore gas is determined, based at least in part, on the absorbed gas NMR signal, the pore gas NMR signal and the gas calibration NMR signal in accordance with one or more embodiments. The gas calibration NMR signal determined by Step 316 and described by Equation (5) may be inserted into Equation (2) to determine the NMR measured fraction volume the absorbed gas. The gas calibration NMR signal may also be and inserted into Equation (3) to determine the NMR measured fraction volume of the pore gas, in accordance with one or more embodiments. The NMR measured fraction volume of the absorbed gas and the NMR measured fraction volume may be written as below respectively as:

$$\phi_{ab} = \frac{\rho_b (d_I^{o.c.})^2 M_{ab}}{\rho_{ab} d_{core}^2 M_{CH_4}^{o.c.}} \quad \text{Equation (7)}$$

$$\phi_p = \frac{\rho_b (d_I^{o.c.})^2 M_p}{\rho_p d_{core}^2 M_{CH_4}^{o.c.}} \quad \text{Equation (8)}$$

By inserting the rock core sample length, l, the total mass of absorbed gas, the total mass of the pore gas and the total injected mass in the rock core sample may be written below respectively:

$$m_{ab} = \rho_{ab} \phi_{ab} d_{core}^2 l = \rho_b (d_I^{o.c.})^2 l \frac{M_{ab}}{M_{CH_4}^{o.c.}} \quad \text{Equation (9)}$$

$$m_p = \rho_p \phi_p d_{core}^2 l = \rho_b (d_I^{o.c.})^2 l \frac{M_p}{M_{CH_4}^{o.c.}} \quad \text{Equation (10)}$$

$$m_{core} = \rho_b (d_I^{o.c.})^2 l \frac{M_{ab} + M_p}{M_{CH_4}^{o.c.}} \quad \text{Equation (11)}$$

By inspecting the Equation (8) and Equation (9) all of the values are either known or have been determined during NMR analysis, including the absorbed gas NMR signal, the pore gas NMR signal and the gas calibration NMR signal. As a result, the absorbed gas and the pore gas may be determined from solving Equation (8) and (9) respectively. The total injected hydrocarbon gas, or total methane mass for this example, is determined by Equation (10).

In Step 320 a reservoir characteristic of the sample is determined, based at least in part, on the mass of the absorbed gas and the mass of the pore gas in accordance with one or more embodiments. The reservoir characteristic may include a porosity, a composition, a water and a hydrocarbon content, a permeability, or a behavior of injected fluid. For example, by using an average rock density, $\rho_{rock}$ to represent the rock core sample, a porosity may be determined in accordance with one or more embodiments. The mass of the absorbed gas, the pore gas, and the total injected hydrocarbon gas in 1 ton of rock may be written below respectively as:

$$m_{ab}(1 \text{ ton}) = \frac{4\rho_b (d_I^{o.c.})^2}{\pi \rho_{rock} d_{core}^2} \frac{M_{ab}}{M_{CH_4}^{o.c.}} \quad \text{Equation (12)}$$

$$m_p(1 \text{ ton}) = \frac{4\rho_b (d_I^{o.c.})^2}{\pi \rho_{rock} d_{core}^2} \frac{M_p}{M_{CH_4}^{o.c.}} \quad \text{Equation (13)}$$

$$m_{total}(1 \text{ ton}) = \frac{4\rho_b (d_I^{o.c.})^2}{\pi \rho_{rock} d_{core}^2} \frac{M_{ab} + M_p}{M_{CH_4}^{o.c.}} \quad \text{Equation (14)}$$

where the units for Equations (12), (13), and (14) is ton. If the assumption is made that the pore gas density and the bulk gas density is the same, the porosity of the sample may be written below as:

$$\phi_p = \frac{(d_I^{o.c.})^2 M_p}{d_{core}^2 M_{CH_4}^{o.c.}} \quad \text{Equation (15)}$$

Determining a porosity for the sample, represents one of the reservoir characteristics that may be determined from the embodiments disclosed herein. Traditional NMR analysis that are unable to distinguish a mass of the pore gas from the mass of the absorbed gas may result in determining an inaccurate porosity. The porosity estimation may be too high if the absorbed gas NMR signal is not removed from the NMR spectrum.

In Step 322 a reservoir model is generated using a reservoir modeler based on the reservoir characteristic, in accordance with one or more embodiments. Turning back to FIG. 1, a reservoir modeler may comprise functionality creating a reservoir model to predict the flow of fluids, including hydrocarbon fluids such as oil and gas, through a formation composed of porous, permeable reservoir rocks. The reservoir modeler may combine information determined from well logs, geological models and any reservoir characteristics determined from NMR analyses on rock core samples as described in this method. The reservoir model may include information total hydrocarbon in place, where the hydrocarbons are located, and how effectively the hydrocarbons can potentially flow.

In Step 324 a reservoir simulation is performed, using a reservoir simulator, to determine a drilling target based on the reservoir model. The reservoir model, including information about the total hydrocarbon in place and the ability for that hydrocarbon to flow, may be used as an input to perform a reservoir simulation. A reservoir simulator, described in FIG. 1, may be used to perform a reservoir simulation to predict the behavior of rocks and fluid under various hydrocarbon recovery scenarios, allowing reservoir engineers to understand which recovery options offer the most advantageous hydrocarbon recovery plan for a given reservoir. A drilling target, or a chosen location to penetrate the hydrocarbon reservoir, may be determined through reservoir simulation by estimating the fluid flow within the reservoir given various drilling target scenarios. Drilling decisions including determining an updated drilling target, may be determined based at least part, on the reservoir simulation. In some embodiments, the reservoir modeler and/or the reservoir simulator may include a computer system that is similar to the computer system (602) described below with regard to FIG. 6 and the accompanying description.

In Step 326 a wellbore path may be planned using a wellbore path planning system to intersect the drilling target and a wellbore guided by the wellbore path may be drilled using a drilling system, in accordance with one or more embodiments. Prior to the commencement of drilling, a wellbore plan may be generated. The wellbore plan may include a starting surface location of the wellbore, or a subsurface location within an existing wellbore, from which the wellbore may be drilled. Further, the wellbore plan may include a terminal location that may intersect with the targeted hydrocarbon bearing formation and a planned wellbore path from the starting location to the terminal location. A wellbore planning system may be used to generate the wellbore plan. The wellbore planning system may comprise one or more computer processors in communication with computer memory containing the reservoir model, information relating to drilling hazards, and the constraints imposed by the limitations of the drillstring and the drilling system.

FIGS. 4A-4C show three NMR spectra measured using the embodiments described herein. FIGS. 4A, 4B and 4C display a chemical shift determined from the NMR test on the horizontal axis (404) and intensity of NMR response on the vertical axis (402). The baseline NMR spectrum (406) and the saturated NMR spectrum (408) were determined from the same NMR system with consistent experimental parameters. These experimental parameters include the same size and type of pressure cell, NMR coil and Rf pulse used to excite the system. The differential NMR Spectrum (412) results from the subtraction of the baseline NMR spectrum (406) from the saturated NMR spectrum (408). The sample used in the NMR analysis was cored from a shale formation known to be a hydrocarbon source rock with a kerogen matrix having a diameter of $1/8^{th}$ inch (3.4 mm) and a length of $17/8^{th}$ inch (48 mm).

FIG. 4A shows a baseline NMR spectrum (406) of the pressure cell containing the sample. FIG. 4A shows the NMR spectrum obtained using traditional NMR analyses without the injection of a gas into the system and is described by Step 302. This baseline NMR spectrum (406) represents the NMR response from the rock core sample. Prior to obtaining the baseline NMR spectrum (406), the sample may be vacuumed to remove any removable fluid from the surface and pore space of the sample. By removing the fluid material from the pore space of the rock, the pore space of the rock core sample is free to accept a hydrocarbon gas. The rock core sample is placed inside a pressure cell and placed in the center of two superconducting magnets, illustrated in FIG. 2. An Rf pulse is used to excite the system, producing and FID signal. This FID signal is transformed by the NMR control and data acquisition system, into an interpretable baseline NMR spectrum. The baseline NMR spectrum (406) is displayed with chemical shift on the horizontal axis (404) and intensity of NMR response on the vertical axis (402). The baseline NMR spectrum (406) is characterized by having a broad region (414) and an absence of a sharp peak.

The saturated NMR spectrum (408), displayed in FIG. 4B, was measured with an embodiment of the method outlined in Step 306. The saturated NMR spectrum (408) is displayed with chemical shift on the horizontal axis (404) and intensity of NMR response on the vertical axis (402). The saturated NMR spectrum (408) was recorded using the same rock core sample used to determine the baseline NMR spectrum (406) previously. The rock core sample has had the removable fluid vacuumed from its surface and pore space and becomes a saturated sample following the injection of a hydrocarbon gas into the pressure cell containing the sample. Methane gas injected at a predetermined measurement pressure of 1000 psi, was used to establish the predetermined measurement pressure and saturate the sample. Once the sample is fully saturated, the saturated NMR spectrum (408) is recorded. The saturated NMR spectrum (408) represents the NMR response of the rock core sample, the pore gas, and the absorbed gas in accordance with one or more embodiments. The combination of pore gas and absorbed gas is referred to as a total gas. The baseline NMR spectrum (406) is characterized by having a broad region (414) a narrow peak (416) and a broad peak (410). The broad region (414) represents the NMR response from the rock core sample, the narrow peak (416) represents the NMR response from the pore gas and the broad peak (410) represents the NMR response from the absorbed gas.

The differential NMR spectrum (412), displayed in FIG. 4C, was measured with an embodiment of the method outlined in Step 308. The differential NMR spectrum (412) is determined by subtracting the baseline NMR spectrum (406) from the saturated NMR spectrum (408) in accordance with one or more embodiments. The baseline NMR spectrum (406) represents the NMR response from the rock core sample only and the saturated NMR spectrum (408) represents the NMR response from the combination of the rock core sample, the pore gas and the absorbed gas. By subtracting the baseline NMR spectrum (406) from the saturated NMR spectrum (408), the NMR signal that remains, represents the NMR response of the pore gas and the absorbed gas only or the total gas.

The differential NMR spectrum (412) is displayed with chemical shift on the horizontal axis (404) and intensity of NMR response on the vertical axis (402). The baseline NMR spectrum (412) is characterized by a narrow peak (416) and a broad peak (410) and the absence of a broad region. The broad region (414), observable on the baseline NMR spectrum (406) and the saturated NMR spectrum (408) represents the NMR response from the rock core sample and has been removed from the differential NMR spectrum (412). The differential NRM spectrum (412) therefore has separated the total gas NMR response from the rock core sample NMR response. The differential NMR spectrum (412) is said to have an overlapping NMR response containing the NMR signal from the pore gas and the NMR signal from the absorbed gas.

A spectral deconvolution may be performed to separate the differential NMR spectrum (418) into an absorbed gas NMR spectrum and a pore gas NMR spectrum according to Step 310. A nonlinear least squares curve fitting application was used to fit the broad peak (410) of the differential NMR spectrum (412) to a first Lorentzian curve (420) and to fit the narrow peak (416) to a second Lorentzian curve (418). Curve fitting may be done by manually by a user using the NMR control and data acquisition system or the NMR control and data acquisition system may include hardware or software with functionality for automatically curve fitting the differential NMR spectrum. The first Lorentzian curve (420) used to fit the broad peak represents the absorbed gas NMR spectrum in accordance with one or more embodiments. The second Lorentzian curve (418) is fit to the narrow peak of the differential NMR spectrum (412) and represents the pore gas NMR spectrum in accordance with one or more embodiments. The two peaks (410,416) on a differential NMR spectrum (412) fit by two Lorentzian curves (420,418) are illustrated in FIG. 4C in accordance with one or more embodiments.

Once separated, the absorbed gas NMR signal is determined based on the absorbed gas NMR spectrum and the pore gas NMR signal is determined based on the pore gas NMR signal according to Step 312. A normalization NMR spectrum of a pressure cell containing a gas injected at a predetermined measurement pressure is then acquired to determine a gas calibration NMR signal according to Steps 314 and 316. The mass of the absorbed gas and the mass of the pore gas is determined, based at least in part, on the absorbed gas NMR signal, the pore gas NMR signal and the gas calibration NMR signal in accordance with Step 318. A reservoir characteristic may be determined based, at least in part, on the mass of the absorbed gas and the mass of the pore gas in accordance with one or more embodiments. The reservoir characteristic may include a porosity, a composition, a water and a hydrocarbon content, a permeability, or a behavior of injected fluid.

By differentiating the mass of a pore gas from the mass of an absorbed gas, an improved estimate of a reservoir characteristic may be determined. When the reservoir characteristic is used as a component of a reservoir model forming an input to a reservoir simulator, the improved estimate of the reservoir characteristic may produce a more accurate reservoir simulation of future fluid flow within, and production from, the hydrocarbon reservoir. Decisions, including determining a drilling target, may be determined based on the reservoir simulation.

Figure 5:
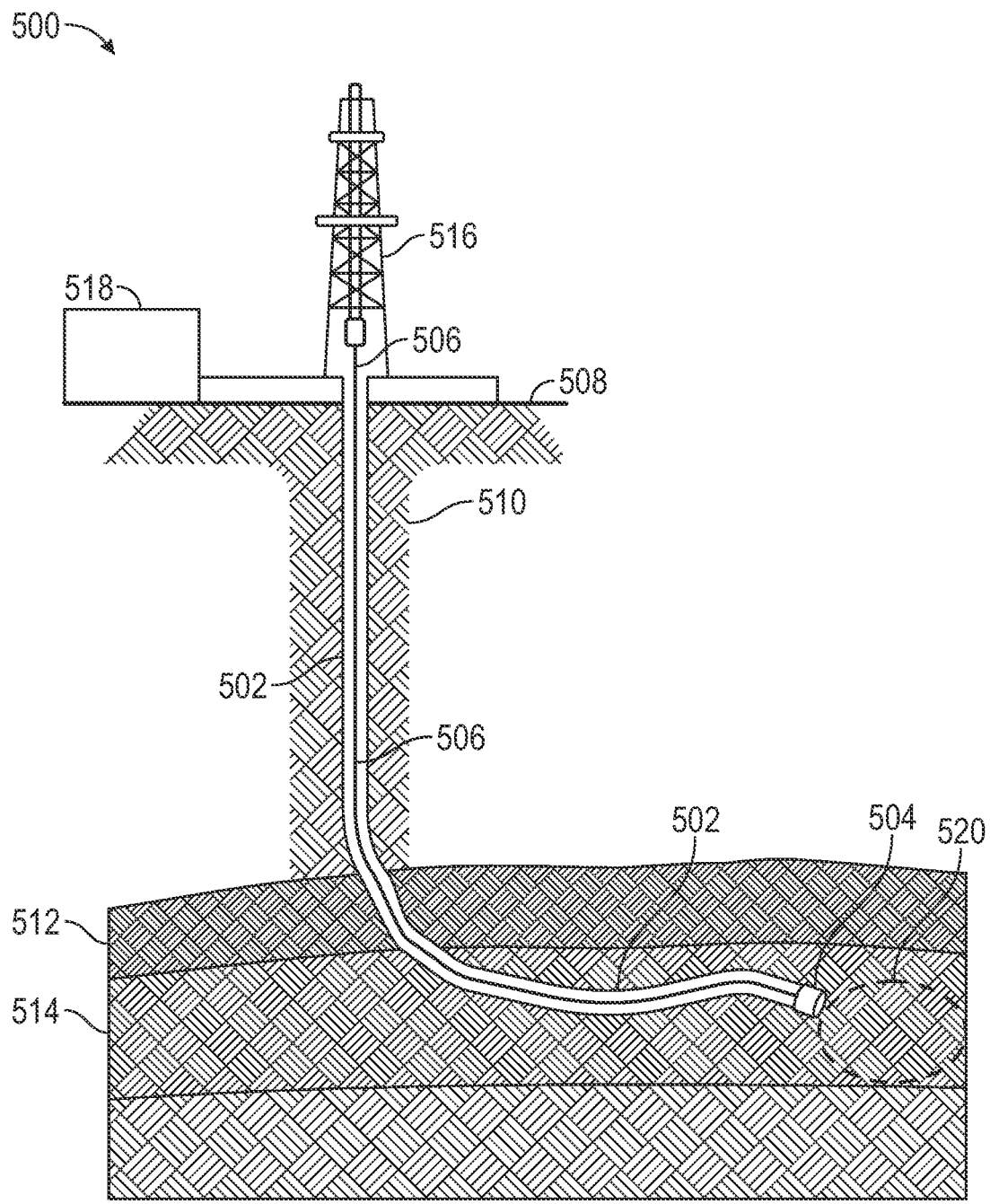
FIG. 5 depicts a drilling system in accordance with one or more embodiments.

FIG. 5 depicts a drilling system (500) in accordance with one or more embodiments. As shown in FIG. 5 a well path (502) may be drilled by a drill bit (504) attached by a drillstring (506) to a drill rig (516) located on the surface of the Earth (508). The well may traverse a plurality of overburden layers (510) and one or more cap-rock layers (512) to a drilling target (520) within a hydrocarbon reservoir (514). The well path (502) may be a curved well path, or a straight well path. All or part of the well path (502) may be vertical, and some well paths may be deviated or have horizontal sections.

Prior to the commencement of drilling, a wellbore plan may be generated. The wellbore plan may include a starting surface location of the wellbore, or a subsurface location within an existing wellbore, from which the wellbore may be drilled. Further, the wellbore plan may include a drilling target (520) and a planned wellbore path from the starting location to the drilling target.

Typically, the wellbore plan is generated based on best available information from a geophysical model associated with the geo-physical properties of the subsurface (e.g., wave speed or velocity, density, attenuation, anisotropy), geomechanical models encapsulating subterranean stress conditions, the trajectory of any existing wellbores (which it may be desirable to avoid), and the existence of other drilling hazards, such as shallow gas pockets, over-pressure zones, and active fault planes. Furthermore, the wellbore plan may take into account other engineering constraints such as the maximum wellbore curvature ("dog-log") that the drillstring may tolerate and the maximum torque and drag values that the drilling system may tolerate.

A wellbore planning system (518) may be used to generate the wellbore plan based on the drilling target (520) determined by the reservoir simulation. The reservoir simulation has predicted the flow of fluids through the reservoir formation, and an advantageous wellbore path to the drilling target (520) may be planned to extract the hydrocarbons. The wellbore planning system (518) may comprise one or more computer processors in communication with computer memory containing the geophysical and geomechanical models, the reservoir simulation, information relating to drilling hazards, and the constraints imposed by the limitations of the drillstring (506) and the drilling system (500). The wellbore planning system (518) may further include dedicated software to determine the planned wellbore path and associated drilling parameters, such as the planned wellbore diameter, the location of planned changes of the wellbore diameter, the planned depths at which casing will be inserted to support the wellbore and to prevent formation fluids entering the wellbore, and the drilling mud weights (densities) and types that may be used during drilling the wellbore.

Figure 6:
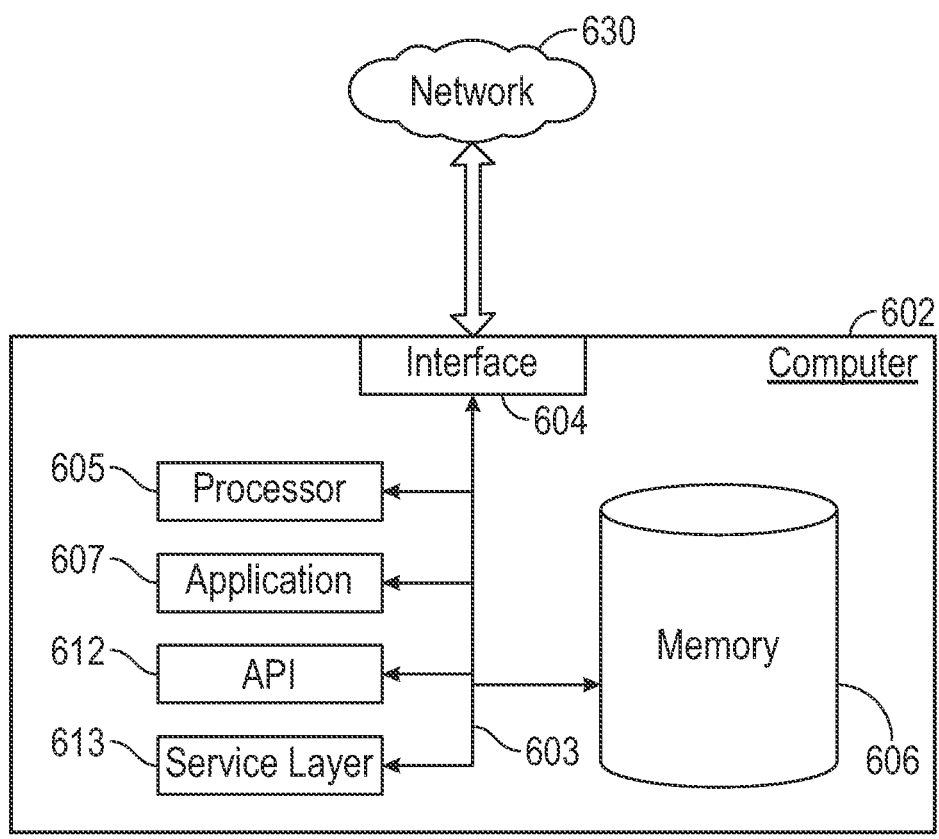
FIG. 6 depicts a computer system in accordance with one or more embodiments.

FIG. 6 depicts a block diagram of a computer system used to provide computational functionalities associated with described algorithms, methods, functions, processes, flows, and procedures as described in this disclosure, according to one or more embodiments. The illustrated computer (602) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (602) may include a computer that includes an input device, such as a keypad, keyboard, touch screen, or other device that can accept user information, and an output device that conveys information associated with the operation of the computer (602), including digital data, visual, or audio information (or a combination of information), or a GUI.

The computer (602) can serve in a role as a client, network component, a server, a database or other persistency, or any other component (or a combination of roles) of a computer system for performing the subject matter described in the instant disclosure. The illustrated computer (602) is communicably coupled with a network (630). In some implementations, one or more components of the computer (602) may be configured to operate within environments, including cloud-computing-based, local, global, or other environment (or a combination of environments).

At a high level, the computer (602) is an electronic computing device operable to receive, transmit, process, store, or manage data and information associated with the described subject matter. According to some implementations, the computer (602) may also include or be communicably coupled with an application server, e-mail server, web server, caching server, streaming data server, business intelligence (BI) server, or other server (or a combination of servers).

The computer (602) can receive requests over network (630) from a client application (for example, executing on another computer (602) and responding to the received requests by processing the said requests in an appropriate software application. In addition, requests may also be sent to the computer (602) from internal users (for example, from a command console or by other appropriate access method), external or third-parties, other automated applications, as well as any other appropriate entities, individuals, systems, or computers.

Each of the components of the computer (602) can communicate using a system bus (603). In some implementations, any or all of the components of the computer (602), both hardware or software (or a combination of hardware and software), may interface with each other or the interface (604) (or a combination of both) over the system bus (603) using an application programming interface (API) (612) or a service layer (613) (or a combination of the API (612) and service layer (613). The API (612) may include specifications for routines, data structures, and object classes. The API (612) may be either computer-language independent or dependent and refer to a complete interface, a single function, or even a set of APIs. The service layer (613) provides software services to the computer (602) or other components (whether or not illustrated) that are communicably coupled to the computer (602). The functionality of the computer (602) may be accessible for all service consumers using this service layer. Software services, such as those provided by the service layer (613), provide reusable, defined business functionalities through a defined interface. For example, the interface may be software written in JAVA, C++, or other suitable language providing data in extensible markup language (XML) format or another suitable format. While illustrated as an integrated component of the computer (602), alternative implementations may illustrate the API (612) or the service layer (613) as stand-alone components in relation to other components of the computer (602) or other components (whether or not illustrated) that are communicably coupled to the computer (602). Moreover, any or all parts of the API (612) or the service layer (613) may be implemented as child or sub-modules of another software module, enterprise application, or hardware module without departing from the scope of this disclosure.

The computer (602) includes an interface (604). Although illustrated as a single interface (604) in FIG. 6, two or more interfaces (604) may be used according to particular needs, desires, or particular implementations of the computer (602). The interface (604) is used by the computer (602) for communicating with other systems in a distributed environment that are connected to the network (630). Generally, the interface (604) includes logic encoded in software or hardware (or a combination of software and hardware) and operable to communicate with the network (630). More specifically, the interface (604) may include software supporting one or more communication protocols associated with communications such that the network (630) or interface's hardware is operable to communicate physical signals within and outside of the illustrated computer (602).

The computer (602) includes at least one computer processor (605). Although illustrated as a single computer processor (605) in FIG. 6, two or more processors may be used according to particular needs, desires, or particular implementations of the computer (602). Generally, the computer processor (605) executes instructions and manipulates data to perform the operations of the computer (602) and any algorithms, methods, functions, processes, flows, and procedures as described in the instant disclosure.

The computer (602) also includes a memory (606) that holds data for the computer (602) or other components (or a combination of both) that can be connected to the network (630). For example, memory (606) can be a database storing data consistent with this disclosure. Although illustrated as a single memory (606) in FIG. 6, two or more memories may be used according to particular needs, desires, or particular implementations of the computer (602) and the described functionality. While memory (606) is illustrated as an integral component of the computer (602), in alternative implementations, memory (606) can be external to the computer (602).

The application (607) is an algorithmic software engine providing functionality according to particular needs, desires, or particular implementations of the computer (602), particularly with respect to functionality described in this disclosure. For example, application (607) can serve as one or more components, modules, applications, etc. Further, although illustrated as a single application (607), the application (607) may be implemented as multiple applications (607) on the computer (602). In addition, although illustrated as integral to the computer (602), in alternative implementations, the application (607) can be external to the computer (602).

There may be any number of computers (602) associated with, or external to, a computer system containing computer (602), wherein each computer (602) communicates over network (630). Further, the term "client," "user," and other appropriate terminology may be used interchangeably as appropriate without departing from the scope of this disclosure. Moreover, this disclosure contemplates that many users may use one computer (602), or that one user may use multiple computers (602).

In some embodiments, an NMR system may perform NMR experiments using a first computer (602) and one or more first Applications (607) while the reservoir simulation may be conducted on a second computer (602) using one or more second Applications (607).

Although only a few example embodiments have been described in detail above, those skilled in the art will readily appreciate that many modifications are possible, including dimensions, in the example embodiments without materially departing from this invention. Accordingly, all such modifications are intended to be included within the scope of this disclosure as defined in the following claims.

What is claimed is:

1. A method of determining a mass of an absorbed gas and a mass of a pore gas in a sample using nuclear magnetic resonance (NMR) spectroscopy, the method comprising:
   acquiring a baseline NMR spectrum of a pressure cell containing the sample;
   creating a gas saturated sample in the pressure cell;
   acquiring a saturated NMR spectrum of the pressure cell containing the gas saturated sample;
   determining a differential NMR spectrum of the sample by subtracting the baseline NMR spectrum from the saturated NMR spectrum;
   separating the differential NMR spectrum into an absorbed gas NMR spectrum and a pore gas NMR spectrum by performing a spectral deconvolution;
   determining an absorbed gas NMR signal based, at least in part, on the absorbed gas NMR spectrum and a pore gas NMR signal based, at least in part, on the pore gas NMR spectrum;
   acquiring a normalization NMR spectrum of the pressure cell containing a gas injected at a predetermined measurement pressure;
   determining a gas calibration NMR signal based, at least in part, on the normalization NMR spectrum; and
   determining the mass of the absorbed gas and the mass of the pore gas based, at least in part, on the absorbed gas NMR signal, the pore gas NMR signal and the gas calibration NMR signal.

2. The method of claim 1, further comprising determining a reservoir characteristic of the sample, based at least in part, the mass of the absorbed gas and the mass of the pore gas, wherein the reservoir characteristic comprises a porosity, a composition, a water and a hydrocarbon content, a permeability, or an injected fluid behavior.

3. The method of claim 2, further comprising:
   generating a reservoir model, using a reservoir modeler based, at least in part, on the reservoir characteristic;
   performing a reservoir simulation, using a reservoir simulator, to determine a drilling target based, at least in part, on the reservoir model;
   planning a wellbore path, using a wellbore path planning system, to intersect the drilling target; and
   drilling a wellbore, guided by the wellbore path, using a drilling system.

4. The method of claim 1, wherein the sample is a rock core sample.

5. The method of claim 1, wherein creating the gas saturated sample in the pressure cell comprises injecting a gas at the predetermined measurement pressure into the pressure cell containing the sample until the saturated NMR spectrum stabilizes.

6. The method of claim 5, wherein the gas is a hydrocarbon gas.

7. The method of claim 1, wherein separating the differential NMR spectrum into the absorbed gas NMR spectrum and the pore gas NMR spectrum by performing the spectral deconvolution comprises:
fitting a first Lorentzian curve to a broad peak of the differential NMR spectrum to obtain the absorbed gas NMR spectrum; and
fitting a second Lorentzian curve to a narrow peak of the differential NMR spectrum to obtain the pore gas NMR spectrum.

8. A non-transitory computer readable memory, having computer-executable instructions stored thereon that, when executed by a processor, perform steps comprising:
acquiring a baseline NMR spectrum of a pressure cell containing a sample;
creating a gas saturated sample in the pressure cell;
acquiring a saturated NMR spectrum of the pressure cell containing the gas saturated sample;
determining a differential NMR spectrum of the sample by subtracting the baseline NMR spectrum from the saturated NMR spectrum;
separating the differential NMR spectrum into an absorbed gas NMR spectrum and a pore gas NMR spectrum by performing a spectral deconvolution;
determining an absorbed gas NMR signal based, at least in part, on the absorbed gas NMR spectrum and a pore gas NMR signal based, at least in part, on the pore gas NMR spectrum;
acquiring a normalization NMR spectrum of the pressure cell containing a gas injected at a predetermined measurement pressure;
determining a gas calibration NMR signal based, at least in part, on the normalization NMR spectrum; and
determining a mass of an absorbed gas and a mass of a pore gas based, at least in part, on the absorbed gas NMR signal, the pore gas NMR signal and the gas calibration NMR signal; and
determining a reservoir characteristic of the sample based, at least in part, the mass of the absorbed gas and the mass of the pore gas.

9. The non-transitory computer readable memory of claim 8, wherein the steps further comprise:
generating a reservoir model using a reservoir modeler based, at least in part, on the reservoir characteristic;
performing a reservoir simulation to determine a drilling target based, at least in part, on the reservoir model; and
planning a wellbore path, using a wellbore path planning system, to intersect the drilling target.

10. The non-transitory computer readable memory of claim 8, wherein the reservoir characteristic comprises a porosity, a composition, a water and a hydrocarbon content, a permeability, or an injected fluid behavior.

11. The non-transitory computer readable memory of claim 8, wherein the sample is a rock core sample.

12. The non-transitory computer readable memory of claim 8, wherein creating the gas saturated sample in the pressure cell comprises injecting a gas at the predetermined measurement pressure into the pressure cell containing the sample until the saturated NMR spectrum stabilizes.

13. The non-transitory computer readable memory of claim 12, wherein the gas is a hydrocarbon gas.

14. The non-transitory computer readable memory of claim 8, wherein separating the differential NMR spectrum into the absorbed gas NMR spectrum and the pore gas NMR spectrum by performing the spectral deconvolution comprises:
fitting a first Lorentzian curve to a broad peak of the differential NMR spectrum to obtain the absorbed gas NMR spectrum; and
fitting a second Lorentzian curve to a narrow peak of the differential NMR spectrum to obtain the pore gas NMR spectrum.

15. A system, comprising:
a pressure cell;
a sample configured to be inserted into the pressure cell;
an NMR pressure and injection system configured to:
establish a predetermined measurement pressure within the pressure cell, and
create a gas saturated sample in the pressure cell; and
an NMR control and data acquisition system configured to:
acquire a baseline NMR spectrum of the pressure cell containing the sample;
acquire a saturated NMR spectrum of the pressure cell containing the gas saturated sample;
determine a differential NMR spectrum of the sample by subtracting the baseline NMR spectrum from the saturated NMR spectrum;
separate the differential NMR spectrum into an absorbed gas NMR spectrum and a pore gas NMR spectrum by performing a spectral deconvolution;
determine an absorbed gas NMR signal based, at least in part, on the absorbed gas NMR spectrum and a pore gas NMR signal based, at least in part, on the pore gas NMR spectrum:
acquire a normalization NMR spectrum of the pressure cell containing the gas saturated sample;
determine a gas calibration NMR spectrum based, at least in part, on the normalization NMR spectrum;
determine a gas calibration NMR signal based, at least in part, on the normalization NMR spectrum;
determine a mass of an absorbed gas and a mass of a pore gas based, at least in part, on the absorbed gas NMR signal, the pore gas NMR signal and the gas calibration NMR signal, and
determine a reservoir characteristic of the sample based, at least in part, on the mass of the absorbed gas and the mass of the pore gas.

16. The system of claim 15, further comprising:
a reservoir modeler configured to produce a reservoir model based, at least in part, on the reservoir characteristic;
a reservoir simulator configured to:
produce a reservoir simulation based, at least in part, on the reservoir model, and
determine a drilling target based, at least in part, on the reservoir simulation;
a wellbore path planning system configured to plan a wellbore path to intersect the drilling target of a subterranean region of interest; and
a wellbore drilling system configured to drill a wellbore guided by the wellbore path.

17. The system of claim 15, wherein the sample is a rock core sample and the reservoir characteristic comprises a porosity, a composition, a water and a hydrocarbon content, a permeability, or an injected fluid behavior.

18. The system of claim 15, wherein creating the gas saturated sample in the pressure cell comprises injecting a gas at the predetermined measurement pressure into the pressure cell containing the sample until the saturated NMR spectrum stabilizes.

19. The system of claim 18, wherein the gas is a hydrocarbon gas.

20. The system of claim 15, wherein separating the differential NMR spectrum into the absorbed gas NMR spectrum and the pore gas NMR spectrum by performing the spectral deconvolution comprises:
   fitting a first Lorentzian curve to a broad peak of the differential NMR spectrum to obtain the absorbed gas NMR spectrum; and
   fitting a second Lorentzian curve to a narrow peak of the differential NMR spectrum to obtain the pore gas NMR spectrum.

* * * * *